(12) United States Patent
Varela-Fuentes et al.

(10) Patent No.: US 7,273,950 B2
(45) Date of Patent: Sep. 25, 2007

(54) PROCESS AND APPARATUS FOR THE EFFICIENT OXIDATION OF ALKYL AROMATIC COMPOUNDS

(75) Inventors: Fernando Varela-Fuentes, Veracruz (MX); Arturo Bulbarela-Croda, Veracruz (MX); Guillermo Ramirez-Aguilar, Veracruz (MX); Bertha Moran-Delgado, Veracruz (MX)

(73) Assignee: Tereftalatos Mexicanos, S.A. de C.V., Veracruz (MX)

( * ) Notice: Subject to any disclaimer, the term of this patent is extended or adjusted under 35 U.S.C. 154(b) by 548 days.

(21) Appl. No.: 10/461,944

(22) Filed: Jun. 13, 2003

(65) Prior Publication Data

US 2004/0254397 A1 Dec. 16, 2004

(51) Int. Cl.
*C07C 51/16* (2006.01)

(52) U.S. Cl. .................................................. 562/412

(58) Field of Classification Search ............... None
See application file for complete search history.

(56) References Cited

U.S. PATENT DOCUMENTS

| 2,962,361 A | 11/1960 | Spiller et al. |
| 3,130,015 A | 4/1964 | Monroe |
| 3,155,718 A | 11/1964 | Brown et al. |
| 3,839,435 A | 10/1974 | Shigeyasu et al. |
| 4,062,654 A | 12/1977 | Shigeyasu et al. |
| 4,159,307 A | 6/1979 | Shigeyasu et al. |
| 4,243,636 A | 1/1981 | Shiraki et al. |
| 4,357,475 A | 11/1982 | Hanotier et al. |
| 4,855,492 A | 8/1989 | Hundley |
| 4,892,970 A | 1/1990 | Nowicki et al. |
| 4,935,539 A | 6/1990 | Lee |
| 5,102,630 A | 4/1992 | Lee |
| 5,371,283 A | 12/1994 | Kingsley et al. |
| 5,536,875 A * | 7/1996 | Roby et al. .................. 562/412 |
| 5,760,288 A | 6/1998 | Asahi et al. |
| 6,175,038 B1 | 1/2001 | Jhung et al. |
| 6,180,822 B1 | 1/2001 | Jhung et al. |
| 6,194,607 B1 | 2/2001 | Jhung et al. |
| 2004/0234435 A1 | 11/2004 | Bickham et al. |

OTHER PUBLICATIONS

Warren L. McCabe & Julian C. Smith, Unit Operations of Chemical Engineering (International student edition © Jul. 7, 1965), © 1956, McGraw-Hill, Inc., Mexico City Mexico.

* cited by examiner

*Primary Examiner*—Paul A. Zucker
(74) *Attorney, Agent, or Firm*—Frommer Lawrence & Haug LLP; A. Thomas S. Safford

(57) ABSTRACT

A method and apparatus for the conversion of aromatic alkyls to aromatic carboxylic acids in a reactor are provided, wherein the location of the feeding of the reaction mixture into the reactor significantly increases the conversion efficiency of the precursor materials.

21 Claims, 3 Drawing Sheets

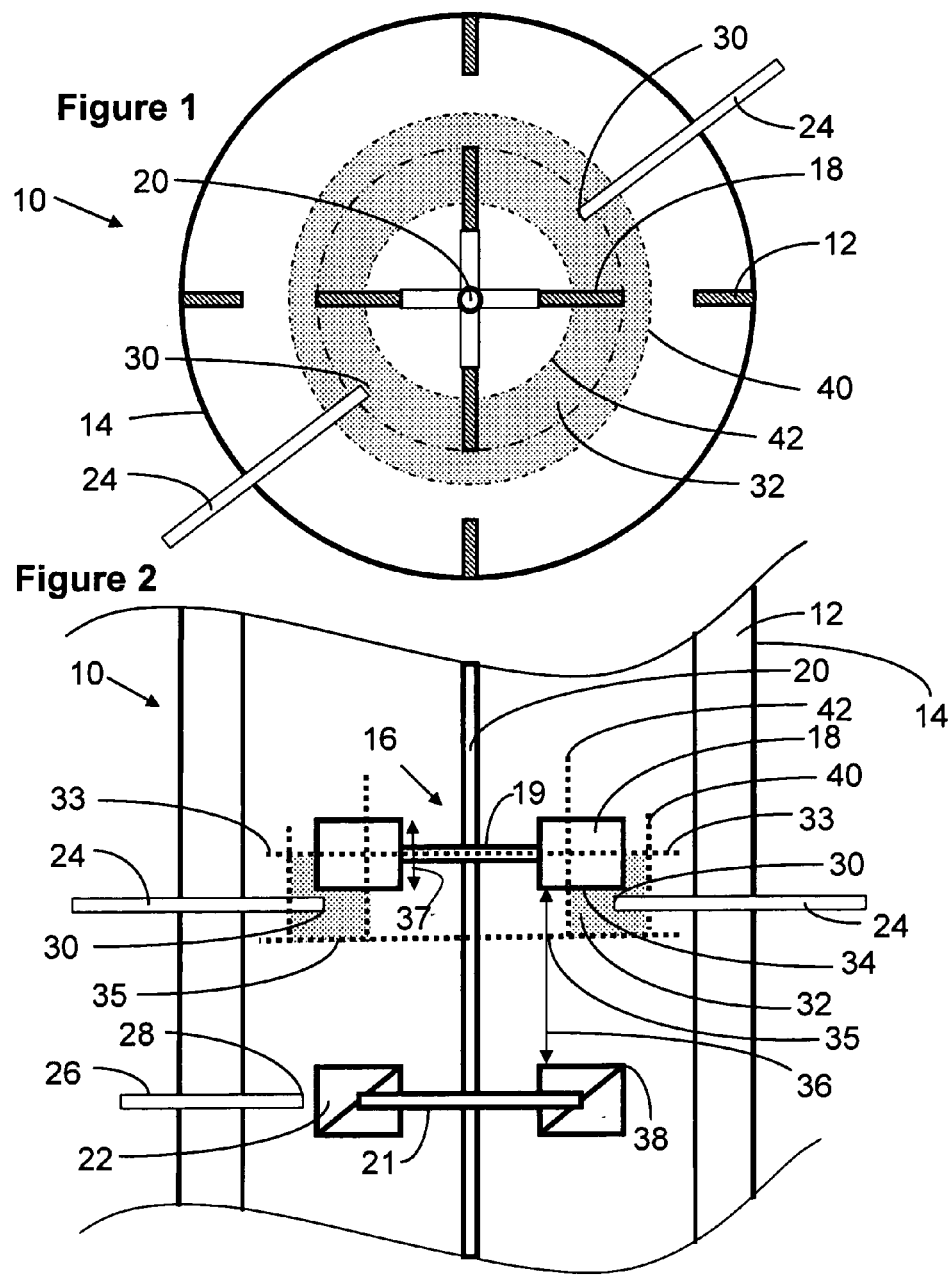

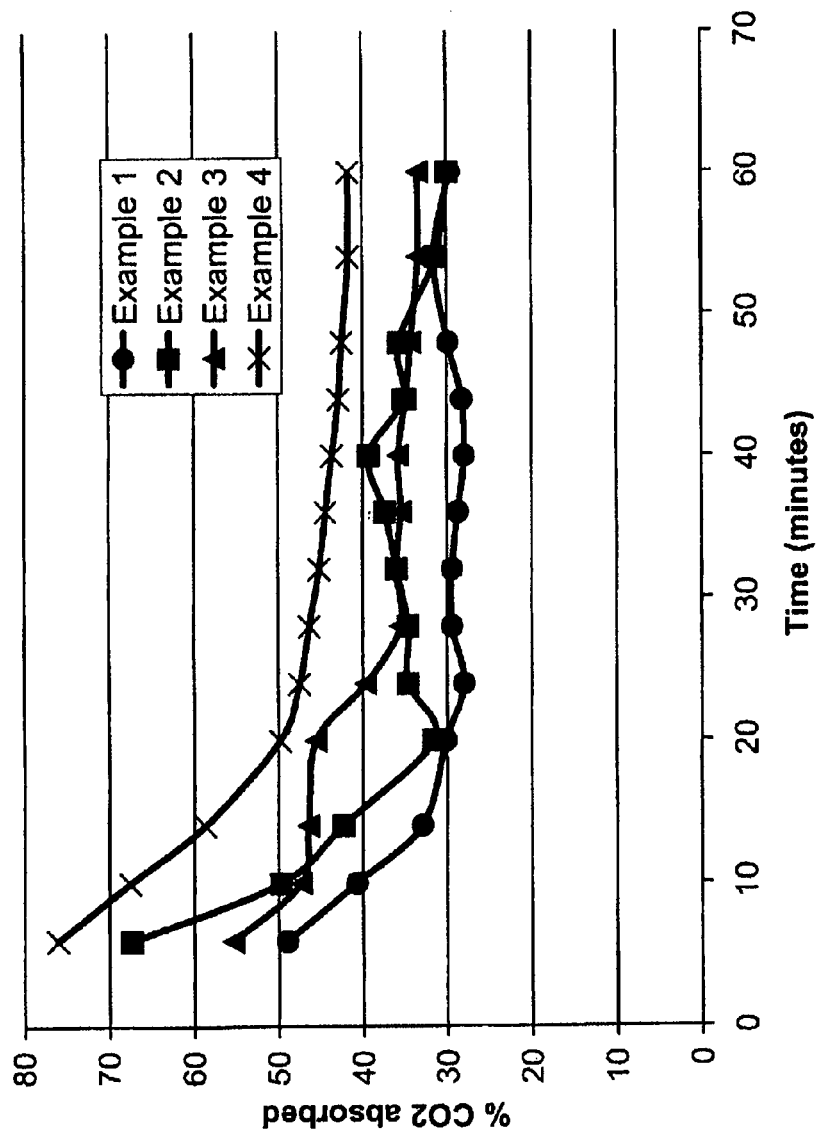

PROCESS AND APPARATUS FOR THE EFFICIENT OXIDATION OF ALKYL AROMATIC COMPOUNDS

FIELD OF THE INVENTION

The present invention relates to a continuous, liquid-phase oxidation of an aromatic alkyl compound to an aromatic carboxylic acid. More particularly, the present invention relates to feeding a reaction mixture into a stirred oxidation reactor at specific locations, thereby increasing the efficiency of the oxidation reaction.

Documents cited in this text, and all documents cited or referenced in the documents cited in this text, are incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

BACKGROUND OF THE INVENTION

Liquid-phase oxidation of an aromatic alkyl to an aromatic carboxylic acid is a highly exothermic chemical reaction. Volatile aqueous acidic solvents are typically used to contain the reaction mixture and to dissipate the heat of reaction. The oxidation of aromatic alkyls is generally performed with a mixture of an ionic catalyst, such as cobalt, manganese, and bromine. Preferred ionic catalysts are cobalt acetate, manganese acetate hydrobromic acid, cobalt and manganese bromide, or any other form that makes available the ionic forms of these elements in the reaction medium.

The preferred oxidation solvent is a low molecular weight aliphatic mono-carboxylic acid having 2 to 6 carbon atoms, inclusive, or mixtures thereof with water. An example of such a solvent is acetic acid, or mixtures of acetic acid and water. Some U.S. patents relate to processes using other solvents, for example, U.S. Pat. Nos. 4,357,475, 4,892,970, and 5,760,288. A reaction temperature of 145° C. to 235° C. is typical, and the reaction pressure is such that the reaction mixture is kept under liquid phase conditions. A promoter such as a low molecular weight ketone having 2 to 6 carbon atoms or a low molecular weight aldehyde having 1 to 6 carbon atoms can also be used. Bromine promoter compounds known in the art, such as hydrogen bromide, molecular bromine, sodium bromide and the like can also be used. A source of molecular oxygen is also used for the conversion of p-xylene to terephthalic acid. It can vary in molecular oxygen content from that of 10% molecular oxygen, to oxygen gas, as shown for example in U.S. Pat. Nos. 5,371,283, 6,175,038 B1, 6,180,822 B1, and 6,194,607 B1.

Air is the preferred source of molecular oxygen. In order to avoid the formation of explosive mixtures, however, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen, measured on a solvent-free basis, in the overhead gas-vapor mixture, as noted in U.S. Pat. Nos. 2,962,361 and 3,155,718.

U.S. Pat. No. 3,839,435 (the "'435 patent") relates to ways of feeding a reaction mixture and the location of the delivery of the reaction mixture into an oxidation reactor. A reactor comprising four levels of Rushton-type agitator is shown wherein reactants are fed through separate feeding pipes to zones close to the impellers. As recited in the '435 patent, p-xylene is fed through pipes $3a$, $3b$ and $3c$ to a zone near the upper edge of the first, second and third levels of impellers; the mixture of solvent and catalyst is fed through pipe 4 to a point in the upper half portion of the reactor and the recycled stream of condensed solvent is fed through pipe 10 to a point in the lower half of the reactor. The oxygen containing gas is introduced through pipe 5 to the bottom of the reactor below the lowest level of impellers so that the gas bubbles ascend through the liquid phase reactants. The '435 patent notes that the quality of the terephthalic acid produced is influenced by the manner of supplying p-xylene into the reaction zone; and, therefore, the '435 patent proposes to feed p-xylene through at least three inlets located and distributed in the vertical direction inside the reactor, and that it is desirable to supply the p-xylene through the inlets as near as possible to the end of the blades of a stirrer. The '435 patent, however, requires at least three feeding pipes for only one reactant, which results in a complex configuration.

U.S. Pat. No. 4,062,654 relates to a reaction vessel for producing an aromatic carboxylic acid by liquid-phase oxidation with a molecular oxygen-containing gas, wherein solvent is sprayed by means of a porous plug or a perforated ring to prevent the adhesion of the aromatic carboxylic acid to the inside wall of the reactor. The materials are fed to the reactor at non-specific points located above a one stage impeller. There is no teaching in this patent about specific feed locations to improve the conversion efficiency.

U.S. Pat. No. 4,159,307 relates to an apparatus for producing an aromatic dicarboxylic acid by oxidizing a benzene derivative with molecular oxygen in the liquid phase, wherein the starting material is fed into the liquid phase in a uniformly dispersed state by being passed through a porous material causing the pressure of the starting material liquid do to drop more than 1 Kg/m². There is no teaching in this patent about specific feed locations to improve the conversion efficiency.

U.S. Pat. No. 4,243,636 relates to an oxidation reactor comprising tooth-like stirring elements in the form of comb-like agitating blades. The reacting mixture is fed through a pipe to a point located at the bottom of the reactor and the product is withdrawn through a pipe located at the upper portion of the reactor. There is no teaching in this patent about specific feed locations to improve the conversion efficiency, but is addressed to the form of the agitating blades.

It is desirable, therefore, to provide a process and an apparatus for the conversion of an aromatic alkyl to a carboxylic acid in an oxidation reactor, wherein the reactor has a simple and low-cost design. None of the above documents discloses the combination of features and advantages of the present invention.

OBJECTS AND SUMMARY OF THE INVENTION

Therefore an object of the invention can be to provide an improved process and apparatus for obtaining an increased efficiency of chemical reactions between reactants in a gas phase dispersed within a liquid-phase by agitation.

Another object of the invention can be to provide an improved stirred reactor design of the type having a catalytic liquid-phase medium for efficient liquid-phase oxidation of alkyl aromatic compounds with molecular oxygen.

A further object of the invention can be to provide an improved process for production of carboxylic acids such as terephthalic acid.

Additional objects of the invention will be pointed out below or will be evident to those skilled in the art from this text. More specifically, various other objects, advantages and features of the present invention will become readily apparent from the ensuing detailed description and the novel features will be particularly pointed out in the appended claims. However, objects of the invention are not to be considered limitations of the invention.

In accordance with the present invention, a method is provided for performing a chemical reaction, comprising dispensing a liquid into a reactor, said reactor comprising a hollow vessel with inner and outer walls and an agitation element positioned within said hollow vessel, said agitation element comprising a rotable shaft having top and bottom ends, said rotable shaft adapted to receive an uppermost set of impellers substantially at the top end, and a lowermost set of impellers substantially at the bottom end, wherein both of said uppermost and lowermost sets of impellers comprise a plurality of blades having upper and lower edges, whereby said set of uppermost impellers is substantially immersed in the liquid; and feeding a reactant into the liquid at a feeding point in a zone located proximate to said uppermost set of impellers, wherein the zone is vertically defined by an upper limit defined by a line perpendicular to said shaft and passing through about half the height of the uppermost set of impeller blades and by a lower limit defined by a line perpendicular to said shaft and located below the lower edge of said uppermost impeller blades at about ⅓ the distance from the lower tip of the uppermost set of impeller blades to said lowermost set of impeller blades, measured downwards from said lower edge of said uppermost impeller blades and radially defined by an outer circle line located at about 0.1 times the vessel diameter measured from the tip of said uppermost set of impellers towards the inner wall of said reactor and an inn er circle line located at about ⅔ of the radius of said uppermost set of impeller blades measured from said shaft towards the impeller outer tip of said uppermost set of impeller blades.

Further in accordance with the present invention, a method is provided for performing a chemical reaction by dispersing a gas within a liquid, comprising the steps of: utilizing a reactor comprising a hollow vessel having inner and outer walls and an agitation element within said hollow vessel, said agitation element comprising a rotable shaft having top and bottom ends, said rotable shaft adapted to receive an uppermost set of impellers substantially at the top end, and a lowermost set of impellers substantially at the bottom end, wherein both of said uppermost and lowermost sets of impellers comprise a plurality of blades having upper and lower edges; dispensing a liquid into said reactor to a level within said reactor such that said uppermost set of impellers of said agitation element is substantially immersed in said liquid; and feeding a reactant into said liquid at a feeding point located below said uppermost set of impellers in a zone, said zone: vertically defined by the arc described by the lower tip of the uppermost set of impeller blades and at about ⅓ the distance from the lower tip of the uppermost set of impeller blades to said lowermost set of impeller blades, and radially defined by an area between 0.1 times the vessel diameter measured from the tip of said uppermost set of impellers towards the inner wall of said reactor to about ⅓ of the diameter of said uppermost set of impeller blades measured from the impeller tip of said uppermost set of impeller blades to said shaft.

Additionally, and in accordance with the present invention, an apparatus is provided for oxidizing an alkyl aromatic compound into an aromatic carboxylic acid, comprising: a hollow vessel with inner and outer walls; an agitation element positioned within said hollow vessel, said agitation element comprising a rotable shaft having top and bottom ends, said rotable shaft adapted to receive an uppermost set of impellers substantially at the top end, and a lowermost set of impellers substantially at the bottom end, wherein both of said uppermost and lowermost sets of impellers comprise a plurality of blades having upper and lower edges; means for feeding a reaction mixture into said reactor in a feeding zone in said reactor: vertically defined by an upper limit defined by a line perpendicular to said shaft and passing through about half the height of the uppermost set of impeller blades and by a lower limit defined by a line perpendicular to said shaft and located below the lower edge of said uppermost impeller blades at about ⅓ the distance from the lower tip of the uppermost set of impeller blades to said lowermost set of impeller blades, measured downwards from said lower edge of said uppermost impeller blades; and radially defined by an outer circle line located at about 0.1 times the vessel diameter measured from the tip of said uppermost set of impellers towards the inner wall of said reactor, and an inner circle line located at about ⅔ of the radius of said uppermost set of impeller blades measured from said shaft towards the impeller outer tip of said uppermost set of impeller blades; means for feeding an oxidizing agent at a feeding point located substantially near the lowermost set of impellers; and means for withdrawing a solid product from said reactor at a point below said lowermost set of impellers. The means for feeding the reaction mixture substantially does not come into contact with the agitation element.

Still further, and in accordance with the present invention, a method for performing a chemical reaction by feeding a reactant into a liquid is provided, comprising the steps of: utilizing a reactor comprised of a hollow vessel having inner and outer walls and an agitation element within said hollow vessel, said agitation element comprising a rotable shaft having top and bottom ends, said rotable shaft adapted to receive an uppermost set of impellers substantially at the top end, and a lowermost set of impellers substantially at the bottom end, and a third set of impellers positioned substantially equidistant between said uppermost and said lowermost sets of impellers, wherein said uppermost, lowermost and third sets of impellers comprise a plurality of blades having upper and lower edges; establishing a liquid into said reactor to a level within said reactor such that said uppermost set of impellers of said agitation element is substantially immersed in said liquid; and feeding a reactant into said liquid at a feeding point in a zone located just below said uppermost set of impellers, said zone being: vertically defined by an upper limit defined by a line perpendicular to said shaft and passing through about half the height of the third set of impeller blades and by a lower limit defined by a line perpendicular to said shaft and located below the lower edge of said third set of impeller blades at about ⅓ the distance from the lower tip of the third set of impeller blades to said lowermost set of impeller blades, measured downwards from said lower edge of said third set impeller blades; and radially defined by an outer circle line located at about 0.1 times the vessel diameter measured from the tip of said third set of impellers towards the inner wall of said reactor, and an inner circle line located at about ⅔ of the radius of said inner set of impeller blades measured from said shaft towards the impeller outer tip of said third set of impeller blades.

Additionally still, and in accordance with the present invention, a reactor for oxidizing an alkyl aromatic compound into an aromatic carboxylic acid is provided, comprising: a reaction vessel with an inner wall; an agitation element positioned within said hollow vessel, said agitation element comprising a rotable shaft having top and bottom ends, said rotable shaft adapted to receive an uppermost set of impellers substantially at the top end, a lowermost set of impellers substantially at the bottom end, and a third set of impellers positioned substantially equidistant between said uppermost and said lowermost sets of impellers, wherein said uppermost, lowermost and third sets of impellers comprise a plurality of blades having upper and lower edges; means for feeding a reaction mixture into said reactor in a feeding zone in said reactor: vertically defined by an upper limit defined by a line perpendicular to said shaft and passing through about half the height of the third set of impeller blades and by a lower limit defined by a line perpendicular to said shaft and located below the lower edge of said third set of impeller blades at about ⅓ the distance from the lower tip of the third set of impeller blades to said lowermost set of impeller blades, measured downwards from said lower edge of said third set impeller blades; and radially defined by an outer circle line located at about 0.1 times the vessel diameter measured from the tip of said third set of impellers towards the inner wall of said reactor, and an inner circle line located at about ⅔ of the radius of said inner set of impeller blades measured from said shaft towards the impeller outer tip of said third set of impeller blades, means for feeding an oxidizing agent at a feeding point located substantially near the lowermost set of impellers; and means for withdrawing a solid product from said reactor at a discharge point at a point below said lowermost set of impellers, wherein said means for feeding said reaction mixture substantially does not come into contact with said agitation element.

In this disclosure, "comprises," "comprising" and the like can have the meaning ascribed to them in U.S. Patent Law and can mean, "includes," "including" and the like.

BRIEF DESCRIPTION OF THE DRAWINGS

In this specification and the accompanying drawings, some preferred embodiments of the invention are shown and described, and various alternatives and modifications thereof have been suggested. It is to be understood that these are not intended to be exhaustive and that many other changes and modifications can be made within the scope of the invention.

The suggestions herein are selected and included for purposes of illustration in order that others skilled in the art will more fully understand the invention and the principles thereof and will thus be enabled to modify it in a variety of forms, each as may be best suited to the conditions of a particular use.

In the following detailed description, reference will be made to the accompanying drawings, wherein:

FIG. 1 shows a schematic top, cross-sectional view of a general configuration of a reactor for oxidizing alkyl aromatic compounds illustrating the specific locations of reaction mixture feed according to the invention.

FIG. 2 shows a schematic cross-sectional elevational view of a reactor of FIG. 1 incorporating the invention showing the specific locations of the reaction mixture feed.

Figure 3:
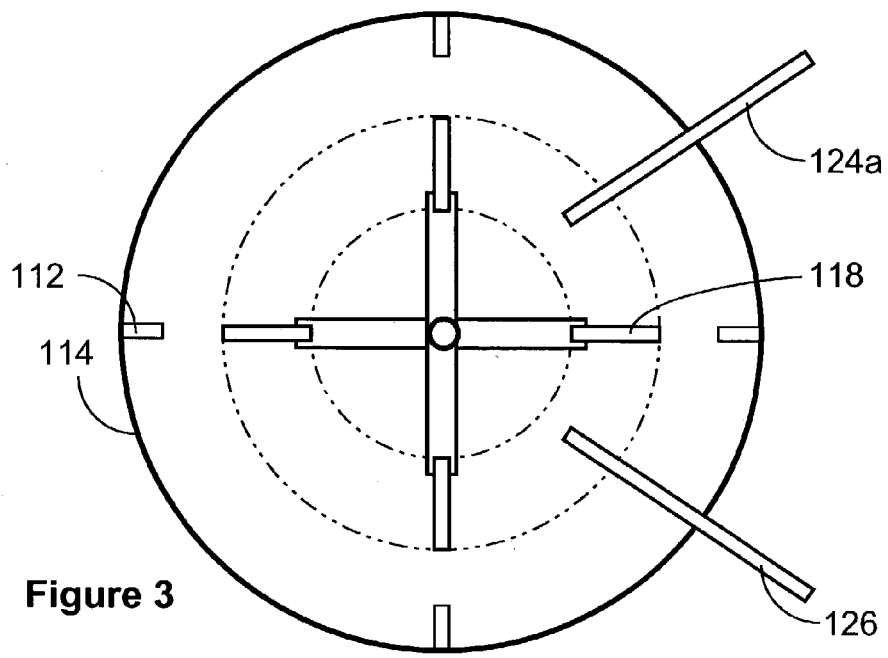

FIG. 3 is a schematic top, cross-sectional view of a test stirred reactor used for determining the preferred locations of the feed points of reaction mixture.

Figure 4:
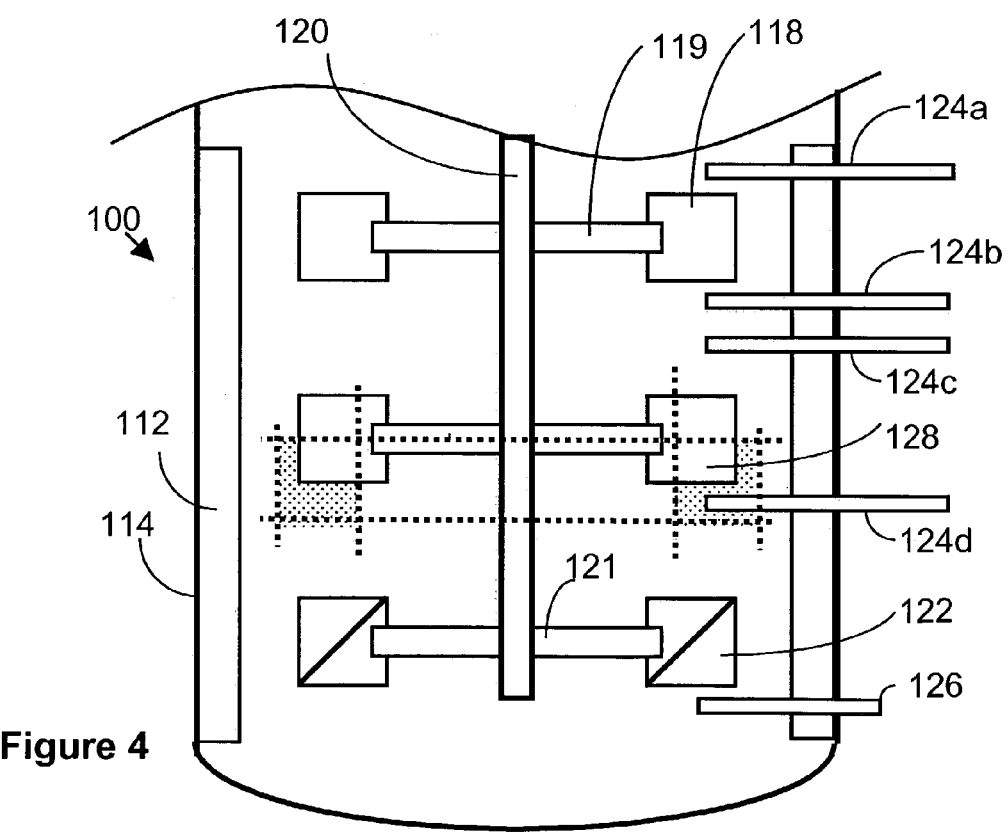

FIG. 4 is a schematic cross-sectional elevational view of the test stirred reactor of FIG. 3 used for determining the preferred locations of the feed points of reaction mixture.

FIG. 5 is graph illustrating the results of the tests made in the a reactor comparing the efficiency of a liquid-gas reaction for several locations of the reactants feed inside the reactor.

DETAILED DESCRIPTION OF ILLUSTRATIVE PREFERRED EMBODIMENTS OF THE INVENTION

The embodiments of the present invention can be used to perform more effective oxidative conversion of an aromatic compound into a carboxylic acid. The aromatic compounds useful to be oxidized by the process and apparatus of this invention, also known as "aromatic feedstock," are any aromatic compounds that have oxidizable constituents, such as alkyl groups. Examples of alkyl groups include methyl, ethyl, or isopropyl group, which can be oxidized to a corresponding carboxylic acid group. The aromatic compound can also have a partially oxidized alkyl group such as an alcohol group, aldehyde group or ketone group. The aromatic portion of the aromatic feedstock compound can be a benzene nucleus or bi- or polycyclic nucleus, for example a naphthalene nucleus. The number of oxidizable constituents usually ranges from 1 to 4, preferably from 2 to 3. Examples of suitable aromatic feedstock compounds for the process of this invention include, but are not limited to, ortho-xylene, meta-xylene, para-xylene, 1,2,4-trimethylbenzene, toluene, ethyl benzene, 1-formyl-4-methylbenzene, 1-hydroxymethyl-4-methylbenzene, 1-formyl-2,4-dimethylbenzene, and the like.

A variety of oxidation catalysts can also be used in the process of the present invention. Preferred catalysts are those metals from the heavy metals group, preferably a mixture of cobalt and manganese. A reaction temperature of 170° C. to 230° C. can be used, said temperature being controlled by means of a pressure control that will maintain the reaction mixture at least partly under liquid phase conditions.

The oxidation is performed in an acidic solvent, or acidic solvent mixture, containing a low molecular weight aliphatic mono-carboxylic acid having 2 to 6 carbon atoms, or mixtures thereof with water. Preferred solvents include, but are not limited to, acetic acid or mixtures of acetic acid and water.

Oxidation promoters can also used in the process of the present invention. A preferred promoter is bromine or compounds comprised of bromine. Examples of bromine promoter compounds include, but are not limited to, hydrogen bromide, molecular bromine, cobalt- or manganese-bromide salts, and the like.

Further, a source of molecular oxygen as the other reactant is also added. Preferably, air is used as the source of molecular oxygen.

In preferred embodiments of the instant invention, alkyl aromatics such as p-xylene, for obtaining terephthalic acid, o-xylene, for obtaining isophthalic acid, 2,6 dimethyl naphthalene, for obtaining 2,6 naphthalene dicarboxylic acid and generally, multi-substituted or monosubstituted alkyl aromatics are fed together with an acidic solvent such as acetic acid, in a solvent/alkyl aromatic weight ratio of from 3:1 to 30:1, preferably from 3.5:1 to 10:1, and more preferably from 4:1 to 8:1. The alkyl aromatic compounds contain a controlled water weight percent, such as, for example, from 3% to 15% water, more preferably from 4% to 10% water, and most preferably from 5% to 10% water. A combination of ion catalysts comprising at least one and preferably at least two of the following ions are used: cobalt, manganese, nickel, chromium and others, a preferred combination being a cobalt/manganese mixture in a ratio of from 0.1: to 20:1, more preferably from 0.5:1 to 10:1 and even more preferably from 0.5:1 to 2:1.

The form in which such catalyst ions are supplied include salts, acetates, bromides or oxides thereof. The ions can also be supplied as metals as long as they are soluble in the reaction media. Further still, aldehydes can also be utilized as catalysts.

The concentration at which these catalysts can be added range from 0.005% to 1.0%, more preferably from 0.01% to 0.6%, but a skilled artisan would readily understand that the concentration is based on, for example, the alkyl aromatic to be oxidized.

Preferably, the reactor utilizes turbine-type impellers, Rushton-type impellers, or combinations thereof. A skilled artisan, however, would readily understand that any impeller in the art can be used.

The reactor vessel can be made of any known material in the art, such as titanium. Preferably, the reactor vessel has a length to diameter ratio of from 1:1 to 1:4, and has from 2 to 8 baffles attached to the inner wall of the vessel. The impeller diameter to reactor diameter ratio is 0.4 to 0.7.

In a preferred embodiment, the reactor of the present invention comprises a configuration wherein the uppermost set of impellers are Rushton-type impellers and the lowermost set of impellers are turbine-type impellers, such as 45° turbine impellers, and wherein the uppermost set of impellers is positioned at a distance of 0.4 to 0.6 times the height of the reactor, and the lowermost set of impellers is positioned at a distance of 0.1 to 0.3 times the height of the reactor.

Preferably, the reactor further comprises a third set of impellers positioned substantially equidistantly between said uppermost and said lowermost sets of impellers, wherein the third set of impellers are Rushton-type impellers. In such a configuration, the uppermost set of impellers is positioned at a distance of 0.5 to 0.7 times the height of the reactor, said lowermost set of impellers is positioned at a distance of 0.1 and 0.3 times the height of said reactor, and said third set of impellers is positioned at a distance of 0.3 to 0.6 times the height of the reactor. Further still, it is preferable that the reaction mixture is fed through a plurality of feeding pipes distributed around said reactor, most preferably the reaction mixture is fed through 2 to 8 feeding pipes.

Referring to FIGS. 1 and 2, which illustrate a preferred embodiment of the present invention, stirred reactor 10 comprises a plurality of internal baffles 12 attached to inner wall 14. Internal baffles 12 assist in the dispersion of the reactants throughout the reactor vessel. The number of baffles is from 2 to 8. The reactor has a length/diameter (L/D) ratio 1:4, more preferably 1:3, and most preferably 1:2.

Agitation element 16 comprises a stirrer having a combination of at least two sets of dispersion impellers, for example of the Rushton-type impellers, typically with 4 to 6 blades 18, and/or turbine impellers, for example with four or six 45° impellers blades 22. Blades 18 are attached to rotatable shaft 20 by elements 19. Rotable shaft 20 is driven by any suitable driving element known in the art which, for simplicity of this description, is not shown.

In a preferred embodiment of the instant invention, an upper Rushton impeller having blades 18 is located at a height from 0.4 to 0.6 times the total height of the reactor, together with a lower turbine impeller, having blades 22 attached to shaft 20 by elements 21, is located at a height from 0.1 to 0.3 times the total reactor height. Impeller blade 22 has tip 38.

In another embodiment of the instant invention, lowermost turbine impeller with blades 22 is replaced by a Rushton-type impeller (whose blades 18 are attached onto shaft 20 by elements 21).

In still another embodiment (with three sets of impellers as in FIG. 3), two Rushton-type impellers are placed in a position from 0.5 to 0.7 and from 0.3 to 0.6 times the total reactor height respectively, together with a lower turbine impeller placed in a height from 0.1 to 0.3 of the total reactor height. The preferred ratio of impeller diameter to vessel diameter ranges from 0.4 to 0.7, more preferably from 0.5 to 0.6.

The location of the entry point of the aromatic feedstock into the reactor is one of the important features of the instant invention. More specifically, it was discovered that even though it is commonly believed that a reaction mixture is essentially the same in all parts of the liquid volume reactor, this is not the case when performing an alkyl aromatic oxidation process. Applicants have not only confirmed conversion efficiency varies substantially depending on the feed position of the aromatic feedstock; but surprisingly have found a significant improvement over the positioning taught by the '435 patent (which, if anything, teaches away from the present invention). Common practice in the art tends to place the point of entry of the feedstock above the impeller or very close to the upper portion of the arc described by the impeller rotation. Usually this selection of the feed point is based on the belief that a fast and efficient dispersion of alkyl aromatics is necessary for avoiding local high temperature spots with high reaction velocity, conditions that favor acidic solvent loss by combustion and increased by-product formation.

Instead, and as illustrated in FIG. 2, Applicants have discovered that the preferred location for feed point 30 of said aromatic feedstock from pipe 24 is at a point located adjacent to the underside of the uppermost impeller set, preferably in shaded zone 32. Zone 32 is vertically defined by an upper limit defined by a line 33 perpendicular to said shaft 20 and passing through about half the height 37 of the uppermost set of impeller blades 18, and by a lower limit defined by a line 35 perpendicular to said shaft 20 and located below the lower edge 34 of said uppermost impeller blades 18 at about ⅓ the distance 36 from the lower edge 34 of the uppermost set of impeller blades 18 to said lowermost set of impeller blades 22, measured downwards from said lower edge 34 of said uppermost impeller blades 18 and radially in a zone defined by an outer circle line 40 located at about 0.1 times the vessel diameter measured from the tip of said uppermost set of impeller blades 18 towards the inner wall of said reactor 14, and an inner circle line 42 located at about ⅔ of the radius of said uppermost set of impeller blades 18 measured from said shaft 20 towards the outer tip of said uppermost set of impeller blades 18. In a mixing system having more than one Rushton-type impeller, the preferred location of the feed entry point is in the zone below the impeller blades 128 of the lowest Rushton impeller (see FIG. 4).

The oxidation agent is an oxygen-containing source, having an $O_2$ concentration of from 8% to 100%. A preferred oxygen source is air, which is directly fed into the reactor through pipe 26 at a point close to the shearing zone of lowermost impeller with blades 22. In order to avoid potential hazards related to explosive vapor and gas mixture formation in the reactor, the flow rate of air to the reaction system is adjusted so as to reach, in stationary conditions, a residual oxygen content from at least 2% to 8% based on molecular weight.

The oxidation agent is an oxygen-containing source, having an $O_2$ concentration of from 8% to 100%. A preferred oxygen source is air, which is directly fed into the reactor through pipe 26 at a point close to the shearing zone of lowermost impeller 22. In order to avoid potential hazards related to explosive vapor and gas mixture formation in the reactor, the flow rate of air to the reaction system is adjusted so as to reach, in stationary conditions, a residual oxygen content from at least 2% to 8% based on molecular weight.

It has been found that by locating the reaction mixture feed as described above, the presence of alkyl aromatics in the reactor off-gas and vapors is surprisingly and drastically reduced, without affecting the acidic solvent combustion. In other words, the more efficient dispersion of the reactants in the liquid phase of the reactor by the method and apparatus of the present invention results in the increased efficiency of the oxidation reaction. It is believed that the impellers act as a barrier for non-reacted alkyl aromatic feedstock, thereby limiting the flow of the feedstock in the upward direction and allowing for an increased residence time and a more complete reaction process.

EXAMPLES

The following examples are set forth to further describe and illustrate the invention with respect to a three-impeller system. These examples do not impose a limitation on the breadth of the present invention.

Several runs in a test reactor were performed in order to compare the efficiency of the following gas-liquid reaction:

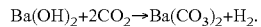

$Ba(OH)_2 + 2CO_2 \rightarrow Ba(CO_3)_2 + H_2$.

Referring to FIG. 3, test reactor 100 was set-up comprising several baffles 112 attached to inner wall 114, agitation element 116 comprising rotating shaft 120 having an uppermost set of impellers with blades 118 attached to shaft 120 by support arm elements 119, and a lowermost set of impellers with blades 122 attached to shaft 120 by support arm elements 121.

The following tests were carried out comparing the location of the feed pipe to the efficiency of the reaction:

Example 1

The test reactor was constructed with a diameter of 24 cm and a height of 50 cm, with a ratio of impeller diameter/vessel diameter of 0.46, and a four-blade, Rushton-type impeller. The reactor was provided with four baffles of a width equal to 0.12 of the vessel diameter. A 0.1% w/w barium hydroxide aqueous solution was dispensed into the reactor vessel, filling the vessel up to a height of 36 cm. A 1.3% barium hydroxide solution was fed continuously at a rate of 166 ml/min to the reactor through pipes 124a see FIG. 4. Also a gas stream of 4% $CO_2$ in $N_2$ solution was fed at a rate of 20 liters/mm through pipe 126. An infrared $CO_2$ measurement cell continuously measured the $CO_2$ concentration in the off-gas. Gas flow and liquid flow rates were continuously monitored by flow measurement elements. The rate of reaction for a first-order barium carbonate precipitation was measured and compared on a relative basis. In all cases the gas was fed through feed line 126 placed 2 cm below lowermost impellers with blades 122 with the discharge tip radially located at a point at ⅓ total impeller diameter, measured from the blade tip towards the central axis of the reactor. In all cases the lower impeller with blades 122 was of the turbine type.

The barium hydroxide solution was fed through a feed line placed 2 cm above uppermost Rushton-type impeller, as shown by pipe 124a, and with discharge ⅓ of the impeller length measured from the arc described by Rushton blade external tip rotation to the impeller axis. Percent $CO_2$ absorbed was measured against time, and the results of the reaction were plotted as illustrated in FIG. 5.

Example 2

With the same reactor arrangement as in Example 1, the barium hydroxide solution was fed 2 cm below upper Rushton impeller as shown by pipe 124b in FIG. 4, while maintaining the same radial location as in previous examples. Percent $CO_2$ absorbed was measured against time, and the results of the reaction were plotted.

Example 3

The reactor arrangement as described in Example 1 above was modified as shown in FIG. 4 to add a third set of impellers with blades 128, Rushton-type, which was placed midway between the uppermost set of Rushton-type impeller with blades 118 and lowermost 45° turbine impeller with blades 122. The barium hydroxide solution was fed midway between both Rushton impellers, as shown by pipe 124c, in a vertical axis measurement, while maintaining the same radial location as in previous examples. Percent $CO_2$ absorbed was measured against time, and the results of the reaction were plotted, as illustrated in FIG. 5.

Example 4

The same mechanical arrangement as described in example 3 was tested, with barium hydroxide solution fed through pipe 124d, with its discharging tip located 2 cm below the middle Rushton impeller and keeping the same radial location as in previous examples. Percent $CO_2$ absorbed was measured against time, and the results of the reaction were plotted.

The results plotted for Examples 1 to 4 were compared. The results indicate that the feed position is one significant factor for the efficiency of gas absorption and conversion in the analogous process for the oxidation of aromatic alkyls to their corresponding carboxylic acids. More specifically, where the percentage of gas $CO_2$ reacted with the liquid reactant barium hydroxide versus time was plotted, the most preferred location for the liquid reactant feed point in a system with three sets of impellers is that of shaded region 32 in FIG. 4 of Example 4.

Example 5

Based on the results of Examples 1 to 4, a titanium reactor was set up having a total volume of 120 liters and an L/D ratio of 1.3, a diameter of 59 cm, and a length of 67 cm. The titanium reactor had the same design characteristics as described in Example 1, with the Rushton-turbine impeller arrangements and a feed point above the uppermost Rushton impeller.

The following tests were carried out with the oxidation reactions of an alkyl aromatic compound:

The test reactor was operated in continuous mode at 15 kg/cm$^2$, pressure Co:Mn ratio of 1:1.3, and Co and Mn concentration of 0.05%. Solvent to alkyl aromatic w/w ratio was 4.0. Water content in the feed was adjusted to 8.0%. Temperature control in the reactor was established according to conditions described in Example 3. The total feed to the reactor was fixed at 42 liters/hr. The p-xylene loss in the vent was measured at 15% to 20% of total p-xylene fed to the reactor.

Example 6

The same equipment configuration and operating conditions as in Example 5 were established, but with feed mixture discharge placed below the uppermost Rushton impeller. The geometric proportions corresponded to those described in Example 1. Upon stabilization of the operation, the p-xylene loss in the vent was measured at 10% of the total p-xylene fed to the reactor.

Example 7

With the same equipment configuration and operating conditions as described in Examples 5 and 6, an impeller system with a Rushton/Rushton-turbine impeller arrangement was installed, with the geometrical proportions described in Example 3. After stable operation, p-xylene concentration in the tower distillate was measured and alkyl aromatic loss was observed to be less than 5% total alkyl aromatic fed to the reactor.

Various modifications and variations of the described compositions, materials and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art or in related fields are intended to be within the scope of the following claims.

What is claimed is:

1. A method for performing a continuous liquid-gas highly exothermic chemical reaction by separately feeding into a stirred liquid medium a gaseous reactant and a liquid reaction mixture, containing at least a liquid reactant, to yield a solid reaction product, comprising the steps of:
   a) utilizing a reactor comprised of a hollow vessel having a cylindrical inner wall with a plurality of vertical baffles extending inwardly and spaced around the inner periphery of the inner wall, an agitation element within said hollow vessel, said agitation element comprising a vertical rotatable shaft, said rotable shaft having a plurality of impellers spaced vertically therealong with each impeller having a plurality of blades with upper and lower edges;
   b) establishing a liquid medium in said reactor to a level within said reactor such that said impellers are immersed in said liquid medium; and
   c) feeding said liquid reaction mixture into said liquid medium at a feeding point in a zone located adjacent the second lowermost impeller, said zone being:
      i) vertically defined by an upper limit defined by a line perpendicular to said shaft and passing through about half the height of the blades of the second lowermost impeller and by a lower limit defined by a line perpendicular to said shaft and located below the lower edge of the blades of the second lowermost impeller at about 1/3 the distance from the lower tip of the blades of the second lowermost impeller to the blades of the lowermost impeller, measured downwards from said lower edge of the blades of the second lowermost impeller; and
      ii) radially defined by an outer circle line located at about 0.1 times the vessel diameter measured from the tip of the blades of the second lowermost impeller towards the inner wall of said reactor, and an inner circle line located at about 2/3 of the radius of the blades of the second lowermost impeller measured from said shaft towards the outer tip of the blades of the second lowermost impeller;
   d) separately feeding said gaseous reactant into said reactor.

2. The method according to claim 1, wherein said second lowermost impeller is of the Rushton-type and at least one of the remaining impellers is of the turbine-type.

3. The method according to claim 2, wherein said chemical reaction is the oxidation to an aromatic carboxylic acid of the liquid reactant by the gaseous reactant which contains molecular oxygen, and which liquid reactant is a compound selected from the group consisting of at least one of an alkyl aromatic compound and a partially oxidized alkyl aromatic compound.

4. The method according to claim 3, wherein number of said impellers range from 2 to 3, and only the lowermost impeller is a turbine-type.

5. The method according to claim 4, wherein said liquid medium comprises liquid reactant; an acidic solvent containing a low molecular weight aliphatic mono-carboxylic acid having 2 to 6 carbon atoms, or a mixture thereof with water; reaction products; and an oxidation catalyst.

6. The method according to claim 5, wherein said liquid reaction mixture comprises, in addition to liquid reactant, an acidic solvent containing a low molecular weight aliphatic mono-carboxylic acid having 2 to 6 carbon atoms, or a mixture thereof with water; and also an oxidation catalyst.

7. The method according to claim 6, wherein said liquid reactant comprises a compound selected from the group consisting of ortho-xylene, meta-xylene, para-xylene, 1,2,4-trimethylbenzene, toluene, ethyl benzene, 1-formyl-4-methylbenzene, 1-hydroxymethyl-4-methylbenzene and 1-formyl-2,4-dimethylbenzene.

8. The method according to claim 7, wherein said acidic solvent in said liquid medium contained in said reactor is comprised of acetic acid or a mixture of acetic acid and water.

9. The method according to claim 8, wherein the ratio of said acidic solvent to said liquid reactant is from 3:1 to 30:1.

10. The method according to claim 9, further comprising 2 to 8 baffles attached to said inner wall.

11. The method according to claim 10, wherein the ratio of the impeller diameter to reactor diameter ranges from 0.4 to 0.7.

12. The method according to claim 11, wherein said reaction mixture is fed through a plurality of feeding pipes distributed around said reactor.

13. The method according to claim 12, further comprising withdrawing a solid product from said reactor at a discharge point at a point below said lowermost impeller.

14. The method according to claim 13, further comprising the steps of feeding said gaseous reactant into a shearing zone at a point near the lowermost impeller in said reactor; and adding an oxidation catalyst into said reactor.

15. The method according to claim 14, wherein said oxidation averages 0.1 to 3 hours, at a temperature of 140-220° C., a pressure of 5-25 bars.

16. The method according to claim 15, wherein said liquid reactant is p-xylene and said product is terephthalic acid.

17. A method for performing a chemical reaction by feeding a reactant into a liquid medium, comprising the steps of:
   a) utilizing a reactor comprised of a hollow vessel having inner and outer walls and an agitation element within said hollow vessel, said agitation element comprising a rotable shaft having top and bottom ends, said rotable shaft adapted to receive an uppermost impeller substantially at the top end, a lowermost impeller substantially at the bottom end, and a third intermediate impeller positioned substantially equidistant between said uppermost and said lowermost impellers, wherein said uppermost, lowermost and intermediate impellers each comprise a plurality of blades having upper and lower edges;
   b) establishing a liquid medium in said reactor to a level within said reactor such that said uppermost impeller of said agitation element is substantially immersed in said liquid medium; and
   c) feeding a reactant into said liquid medium at a feeding point in a zone adjacent said intermediate impeller, said zone being:
      i) vertically defined by an upper limit defined by a line perpendicular to said shaft and passing through about half the height of the intermediate impeller's blades and by a lower limit defined by a line perpendicular to said shaft and located below the lower edge of said intermediate impeller's blades at about ⅓ the distance from the lower tip of the intermediate impeller's blades to said lowermost impeller's blades, measured downwards from said lower edge of said intermediate impeller's blades; and
      ii) radially defined by an outer circle line located at about 0.1 times the vessel diameter measured from the tip of said intermediate impeller towards the inner wall of said reactor, and an inner circle line located at about ⅔ of the radius of said intermediate impeller's blades measured from said shaft towards the outer tip of said intermediate impeller's blades.

18. The method according to claim 17, wherein said chemical reaction is the oxidation to an aromatic carboxylic acid by a gaseous reactant containing molecular oxygen, which reactant is a liquid compound selected from the group consisting of at least one of an alkyl aromatic compound and a partially oxidized alkyl aromatic compound, said gaseous reactant is separately fed to said reactor.

19. The method according to claim 18, wherein said uppermost impeller is positioned at a distance of 0.5 to 0.7 times the height of the reactor, said lowermost impeller is positioned at a distance of 0.1 and 0.3 times the height of said reactor, said intermediate impeller is positioned at a distance of 0.3 to 0.6 times the height of the reactor, said lowermost impeller is a turbine-type and the remaining impellers are Rushton-type, and said gaseous reactant fed into a shearing zone at a point near the lowermost impeller in said reactor.

20. The method according to claim 12, wherein there are two impellers, the uppermost being a Rushton-type impeller and the lowermost being a turbine-type impeller, and wherein said uppermost impeller is position at a distance of 0.4 to 0.6 times the height of the reactor, and said lowermost impeller is positioned at a distance of 0.1 to 0.3 times the height of the reactor.

21. The method according to claim 12, wherein number of impellers is three, the uppermost impeller is positioned at a distance of 0.5 to 0.7 times the height of the reactor, the lowermost impeller is positioned at a distance of 0.1 and 0.3 times the height of said reactor, and the third impeller is intermediately positioned at a distance of 0.3 to 0.6 times the height of the reactor.

* * * * *